United States Patent [19]

Wu

[11] Patent Number: 4,548,905
[45] Date of Patent: Oct. 22, 1985

[54] REAGENT COMPOSITION, DRY ELEMENT AND METHOD FOR DETERMINATION OF TOTAL BILIRUBIN

[75] Inventor: Tai-Wing Wu, Rochester, N.Y.

[73] Assignee: Eastman Kodak Company, Rochester, N.Y.

[21] Appl. No.: 597,881

[22] Filed: Apr. 9, 1984

[51] Int. Cl.⁴ .................. G01N 33/52; G01N 33/72
[52] U.S. Cl. .................................... 436/97; 422/56; 422/57; 436/170
[58] Field of Search ............... 436/97, 169, 170; 422/56, 57, 58

[56] References Cited

U.S. PATENT DOCUMENTS

| | | |
|---|---|---|
| 3,511,607 | 5/1970 | Green . |
| 3,825,411 | 7/1974 | Morin . |
| 3,880,588 | 4/1975 | Rittersdorf et al. . |
| 4,038,031 | 7/1977 | Lam . |
| 4,069,017 | 1/1978 | Wu et al. . |
| 4,098,574 | 7/1978 | Dappen ............................ 436/95 X |
| 4,338,095 | 7/1982 | Wu . |
| 4,468,467 | 8/1984 | Babb et al. ............................ 436/97 |

OTHER PUBLICATIONS

Dappen et al., *Clin. Chem.*, 29(1), pp. 37–41, (1983).
*Fundamentals of Clinical Chemistry*, Tietz (Ed.), W. B. Saunders Co., Philadelphia, pp. 755–760, (1970).
Malloy et al., *J. Biol. Chem.*, 119, p. 481, (1937).

*Primary Examiner*—Arnold Turk
*Attorney, Agent, or Firm*—Lanny Tucker

[57] ABSTRACT

A reagent composition, dry analytical element and a method of using same to determine total bilirubin in aqueous liquids are disclosed. The reagent composition comprises a diazonium salt, or reagents capable of producing a diazonium salt when contacted with water, and 3,3-dimethylglutaric acid or a salt thereof present in an amount effective to buffer the composition at a pH of about 3.5 or less when the composition is contacted with a 2 $\mu$L sample of pooled human serum. The composition and elements described herein provide a means to eliminate the effect of an undetermined interferent which is either preformed or formed in situ in diazo-based total bilirubin determinations of biological fluids (e.g. uremic serum).

20 Claims, No Drawings

REAGENT COMPOSITION, DRY ELEMENT AND METHOD FOR DETERMINATION OF TOTAL BILIRUBIN

FIELD OF THE INVENTION

The present invention relates to a colorimetric assay useful in clinical chemistry for the determination of total bilirubin in aqueous liquids, such as biological fluids. In particular, it relates to a reagent composition, dry analytical element and a method of using same which utilizes a diazonium salt and a particular buffer which maintains a particular pH during the assay.

BACKGROUND OF THE INVENTION

Bilirubin is a degradation product of hemoglobin. Approximately 200 to 230 mg of bilirubin and its derivatives are formed each day in the normal human adult. As part of normal human metabolic processes, the major portion of this daily bilirubin production is excreted or degraded into other derivatives.

Excessive amounts of bilirubin occur within the human body through overproduction of bilirubin as in the case of excessive hemolysis or by retention of bilirubin due, for example, to liver failure. The result of excessive bilirubin within the human body is jaundice. Jaundice is characterized by markedly elevated serum bilirubin levels, for example, 10 mg of bilirubin per dL of serum or higher compared with the normal adult range of 0.1 to about 1 mg of bilirubin per dL of serum. There is increasing evidence that excessive amounts of bilirubin in the blood lead to an undesirable increase in bilirubin concentration within body cells which interferes with various cellular processes. Given this background, the clinical diagnostic significance of bilirubin, in tests for liver and other related organ functions, is self evident.

Perhaps the most widely used assay for bilirubin has been the so called diazo method. In this method, a sample of liquid suspected of containing bilirubin is contacted with a reagent composition which includes a diazonium salt. The diazonium salt reacts with bilirubin to form two azobilirubin fragments. The azobilirubin has an extinction coefficient which is higher than that of bilirubin itself and is therefore easily detectable.

Many diazonium salts have been suggested for use in the diazo method for determining bilirubin. For example, certain 2,4- and 2,5-phenyldiazonium salts (e.g. 2,4- and 2,5-dichlorophenyldiazonium salts) and diazotized sulfanilamide have been used for the detection of bilirubin in serum and urine. However, methods using these diazonium salts are known to be relatively insensitive. Further, some of these diazonium salts, when dry, are explosively unstable, i.e. subject to shock induced decomposition. Thus, handling of these compounds in bilirubin assays, and particularly dry assays, is quite hazardous.

Certain substituted sulfanilamide and carbonamide diazonium salts which are less prone to shock induced decomposition have been found useful in bilirubin assays. These salts and assays are the subject of commonly assigned and copending U.S. Ser. No. 344,433, filed February 2, 1982 by our colleagues, B. E. Babb and G. M. Dappen, and entitled DIAZONIUM SALT FOR BILIRUBIN ASSAY now U.S. Pat. No. 4,468,467. Those salts and assays represent a significant improvement in the clinical chemistry art, overcoming the shortcomings of previously-known bilirubin assays. This improved assay is also described by Babb and co-authors in Clin. Chem., 29(1), pp. 37–41 (1983).

However, there is a need to provide further improvements in the bilirubin assays described and claimed in aforementioned U.S. Pat. No. 4,468,467. With a small percentage of patient serum samples, e.g. those obtained from hemodialysis or other renal-defective patients, interferences were observed to be influential in the end result, detracting from assay accuracy. It is desirable to remove such interferences, thereby providing an assay that is highly accurate with all patient samples including samples obtained from patients having kidney problems.

Known procedures for eliminating interferences in assays include sample pretreatment, sample blanking and polychromatic (i.e. multiple wavelength) analyses. Each of these procedures, however, has its disadvantages. Sample pretreatment is a tedious and imprecise operation and is not readily adaptable to dry chemistry assays. Sample blanking doubles the effort, sample size and cost of each assay and may cause a decrease in precision. The known polychromatic analysis requires pure standards and knowledge of the exact molecular identity or concentrations of predetermined interferents. See, e.g. Hahn et al, Clin. Chem., 25(6), pp. 951–959 (1979).

None of these known procedures has proved effective for eliminating the observed interference in the bilirubin assay described and claimed in U.S. Pat. No. 4,468,467 noted hereinabove. Neither the identity of the interferent nor its concentration (which can vary from sample to sample) is known. This precludes use of the polychromatic analysis which requires knowledge of the interferent or its concentration. The other procedures are equally useless in this instance.

Therefore, there is a need in the art for a diazo bilirubin assay having improved accuracy for all patient samples, which assay overcomes the effect of an undetermined interferent or where the interferent is formed in situ, i.e. during the analysis.

SUMMARY OF THE INVENTION

The present invention provides an improved method of determining total bilirubin. In particular, the present invention provides an accurate analysis of total bilirubin with diazo-based chemistry and overcomes the observed effect of an interferent which is either preformed and undetermined or formed in situ, i.e. during analysis, and is undeterminable. This invention is particularly useful for total bilirubin determination in serum samples obtained from patients requiring hemodialysis or having severe renal disorders, i.e. uremic serum samples.

The advantages of the present invention follow from the use of a particular buffer in the reagent composition and dry element, which buffer maintains a desired low pH, i.e. about 3.5 or less during the assay. There is no ready explanation as to why this particular buffer, 3,3-dimethylglutaric acid or its equivalent salts, overcomes the adverse effect of the interferent in diazo-based bilirubin assays. Other buffers which also provide similarly low pH do not solve the interference problem (see Example 3 hereinbelow).

Therefore, in accordance with this invention, a reagent composition comprises a diazonium salt or reagents capable of producing a diazonium salt when contacted with water, and 3,3-dimethylglutaric acid or a salt thereof present in an amount effective to buffer the composition at a pH of about 3.5 or less when contacted with a 2 μL sample of pooled human serum.

This invention also provides a dry analytical element comprising a carrier matrix, and the reagent composition containing the diazonium salt and the buffer, 3,3-dimethylglutaric acid or a salt thereof, as described hereinabove. In preferred embodiments, the carrier matrix is a support having thereon a porous spreading zone. In such embodiments, the elements can include other zones. The diazonium salt and the buffer can individually be in any zone in the element.

In another aspect, this invention provides a method for determination of total bilirubin in an aqueous liquid. This method comprises the steps of:

(A) physically contacting a sample of the liquid with the reagent composition described hereinabove; and (B) colorimetrically measuring the amount of azobilirubin formed as a result of that contact.

DETAILED DESCRIPTION OF THE INVENTION

The present invention is useful for measuring total bilirubin in an aqueous liquid, such as a biological liquid obtained from an animal or human. For example, total bilirubin can be determined in diluted or undiluted serum, plasma, whole blood, urine, cerebral spinal fluid and other body fluids with this invention. This invention is particularly useful with uremic serum (i.e. serum obtained from hemodialysis or other renal-defective patients).

Bilirubin is detected with this invention using a reagent composition which includes a diazonium salt. This salt reacts with bilirubin to form colorimetrically detectable azobilirubin fragments as noted hereinabove in the Background of the Invention. These salts are often known as diazo reagents by those skilled in the art.

Any of a great number of diazo reagents can be used in the practice of this invention although some, because of their instability in dry form, may be limited in utility to solution or "wet" assays. Examples of useful diazo reagents include 2,6-dichlorobenzenediazonium salts and the like as described, for example, in U.S. Pat. No. 3,880,588 (issued April 29, 1975 to Rittersdorf et al); 2,4-dichlorobenzenediazonium salt and the like as described in U.S. Pat. No. 4,038,031 (issued July 26, 1977 to Lam); diazotized sulfanilic acid; diazotized 2,4-dichloroaniline; diazonium fluoroborate; and others known in the art.

Particularly useful diazonium salts are those described in U.S. Pat. No. 4,468,467, noted hereinabove. Those salts have the advantage of being extremely resistant to shock induced decomposition and therefore, can be used for both solution and dry assays. These diazonium salts are represented by the structure:

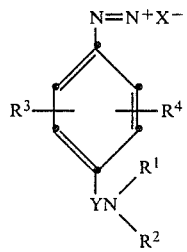

wherein $X^-$ is a stabilizing anion; Y is —CO— or —SO$_2$—; $R^1$ and $R^2$ are independently selected from hydrogen, substituted or unsubstituted alkyl, preferably having from 1 to 20 carbon atoms (e.g. methyl, chloromethyl, isopropyl, dodecyl), substituted or unsubstituted aralkyl, preferably having from 7 to 20 carbon atoms in the aralkyl backbone (e.g. benzyl), substituted or unsubstituted aryl, preferably having from 6 to 14 carbon atoms in the aromatic backbone (e.g. phenyl, xylyl, p-methoxyphenyl, naphthyl), and carboxyalkyl and hydroxyalkyl, preferably wherein the alkyl group is lower alkyl, i.e. having 1 to 4 carbon atoms [e.g. carboxymethyl, carboxyethyl, hydroxymethyl, hydroxyethyl, tris(hydroxymethyl)methyl and hydroxy-4-n-butyl] and more preferably, $R^1$ and $R^2$ are not both hydrogen; and $R^3$ and $R^4$ are independently selected from groups which are electron donor groups or mildly electron withdrawing groups, such that the sum of the Hammett sigma values for $R^3$ and $R^4$ does not exceed +0.4. Examples of such $R^3$ and $R^4$ groups include hydrogen, halogen (e.g. chloro, bromo), lower alkyl preferably of 1 to 4 carbon atoms (e.g. methyl, propyl), alkylthio preferably of 1 to 4 carbon atoms (e.g. methylthio), lower alkoxy preferably of 1 to 4 carbon atoms (e.g. methoxy, ethoxy), aralkoxy preferably of 7 to 10 carbon atoms in the aralkoxy backbone (e.g. benzyloxy), phenylthio, and alkylamino preferably of 1 to 8 carbon atoms (e.g. acetamino). Alternatively, $R^3$ and $R^4$, taken together, represent the carbon atoms necessary to complete a fused carbocyclic arylene moiety, such as naphthylene, indylene, or anthrylene, including such ring structures substituted with the other groups identified for $R^3$ and $R^4$.

Stabilizing anions for these diazonium salts are known. These anions make possible the isolation of the salts in dry form and provide for long term thermal stability as well as reduced shock sensitivity.

In the formula above, $X^-$ is preferably the anion of a Lewis acid coordinatively saturated by a hydrogen halide. Useful stabilizing anions include tetrafluoroborate, hexafluorophosphate, chlorozincate and hexafluorotitanate. Of the preferred anions, hexafluorophosphate has been found to be particularly preferred. Other useful anions include arylsulfonates, such as naphthylene disulfonate and 4,4'-biphenyldisulfonate.

In a particularly preferred embodiment, Y is —SO$_2$—, $R^1$ is hydrogen and $R^2$ is carboxymethyl. These compounds form an azobilirubin which has an extremely high extinction coefficient.

The currently preferred diazonium salt is 4-(N-carboxymethylsulfamyl)benzenediazonium hexafluorophosphate. Other useful compounds include the following:

4-[N,N-bis(carboxymethyl)sulfamyl]benzenediazonium hexafluorophosphate;
4-[N,N-bis(2-hydroxyethyl)sulfamyl]benzenediazonium hexafluorophosphate;
4-(N-carboxymethylcarbamyl)benzenediazonium tetrafluoroborate;
4-(N-carboxypropylcarbamyl)benzenediazonium naphthylenedisulfonate;
4-(N-carboxymethylsulfamyl)benzenediazonium tetrafluoroborate;
4-(N-dodecylsulfamyl)benzenediazonium tetrafluoroborate;
3,5-dichloro-4-(N-carboxymethylsulfamyl)benzenediazonium hexafluorophosphate;
4-(N-carboxymethylsulfamyl)-1-diazonium naphthylene hexafluorophosphate;

7-[N-tris(hydroxymethyl)methylcarbamyl]-4-diazoniumindene hexafluorophosphate; and 4-[N,N-bis(carboxymethyl)sulfamyl]-1-diazonium-6-methoxy naphthylene chlorozincate.

These particularly useful diazonium salts are made by methods which are well known in the art. To illustrate, the preferred sulfonamide compounds are made by first reacting an acetanilide with chlorosulfonic acid to produce N-acetylsulfanilyl chloride. This sulfonyl chloride is then reacted with an amine such as glycine and the N-acetyl group is removed by acid hydrolysis to produce the desired sulfonamide. The sulfonamide is then diazotized using sodium nitrite and an acid such as hydrochloric acid to produce the desired diazonium salt. The desired anion for the diazonium salt is provided by including a salt of the anion in the diazotization reaction mixture. For example, if sodium hexafluorophosphate is included in this reaction mixture, the hexafluorophosphate diazonium salt is produced.

In general, an acid pH ($<7$) is desirable to improve the storage stability of the diazonium salt and to promote the coupling with bilirubin. The reagent compositions described in U.S. Pat. No. 4,468,467 contain any of a variety of acids. However, as noted hereinabove, while it is known that an acidic pH environment ($<7$) is desirable for a bilirubin assay, the problem with an unknown interferent described hereinabove and observed with known assays of uremic patient samples is solved most effectively with the use of 3,3-dimethylglutaric acid or an equivalent alkali metal (sodium, potassium, etc.) or ammonium salt thereof as described herein.

Further, it is essential in the practice of this invention that the 3,3-dimethylglutaric acid or salt thereof is present in the reagent composition in an amount effective to maintain a pH of about 3.5 or less when contacted with a 2 $\mu$L sample of pooled human serum. Preferably, the pH of the composition is maintained between about 1 and about 3.5 when contacted with a 2 $\mu$L sample of pooled human serum. Pooled human serum is a readily available biological product. Although the amount of acid needed for the desired pH can vary with assay conditions (e.g. volume of liquid test sample, type of test sample, solution vs. dry assay), generally 3,3-dimethylglutaric acid (or salt thereof) is present at a concentration of at least about 0.01 M, preferably from about 0.05 M to about 0.5 M, and more preferably from about 0.1 M to about 0.3 M. In assays using dry analytical elements, the acid is generally present in a zone or layer of the element at a coverage of from about 1 to about 7.5, and preferably from about 2.5 to about 5.0, g/m².

In a preferred embodiment of this invention, the described reagent composition includes what is known in the art as a "diazo bilirubin promoter" (sometimes also referred to as an "accelerating agent"). These promoters are compounds which promote the rate of azobilirubin formation. Useful agents include dyphylline, caffeine, sodium acetate, sodium benzoate and gum arabic. Dyphylline is a preferred promoter.

The reagent composition of this invention is prepared in a variety of forms. For example, the reagent composition can be prepared as a lyophilized powder or tablets which are reconstituted with water to produce an aqueous reagent solution which is buffered with the 3,3-dimethylglutaric acid to a pH of 3.5 or less. Techniques for making such forms of reagent compositions and materials such as fillers, binders and the like are well known in the art.

The reagent composition and method of this invention are adaptable to both solution (i.e. "wet chemistry") and dry element (i.e. "dry chemistry") assays. In solution assays, the assay is carried out entirely in a liquid medium by mixing an aqueous liquid sample to be assayed with an aqueous solution containing the reagents. The resulting mixture is incubated at an appropriate temperature if desired. This solution assay technique is well known in the art and is illustrated in more detail hereinbelow in Example 1. In solution assays, the diazonium salt (or diazo reagent) is present in amounts known in the art.

When employed in "dry chemistry" elements, the reagent composition can be incorporated into a suitable carrier matrix by imbibition, impregnation, coating or another suitable technique. Useful carrier matrices are insoluble and maintain their structural integrity when exposed to water or physiological fluids such as urine, serum or whole blood. Useful carrier matrices can be prepared from porous materials such as paper, porous particulate structures, cellulose, wood, glass fiber, woven and nonwoven fabrics (synthetic and nonsynthetic) and the like. A useful dry analytical element is made by imbibing a solution of the reagent composition into the matrix and drying. Useful materials and procedures for making such elements are well known in the art as exemplified in U.S. Pat. Nos. 3,092,465 (issued June 4, 1963 to Adams et al); 3,802,842 (issued April 9, 1974 to Lange et al); 3,915,647 (issued October 28, 1975 to Wright); 3,917,453 (issued November 4, 1975 to Milligan et al); 3,936,357 (issued February 3, 1976 to Milligan et al); 4,248,829 (issued February 3, 1981 to Kitajima et al); 4,255,384 (issued March 10, 1981 Kitajima et al); and 4,270,920 (issued June 2, 1981 to Kondo et al); and U.K. Patent 2,052,057 (published January 21, 1981).

The method of this invention is practiced by physically contacting (e.g. spotting) the element with the aqueous liquid sample (generally 1–20 $\mu$L) to be assayed. The reagent composition is present in such elements as a dried residue (e.g. a freeze-dried powder or dried residue of a coating composition).

The diazonium salt is generally present in the elements of this invention at a coverage of at least about 0.05 g/m², and preferably at a coverage of from about 0.2 to about 2 g/m².

Preferably, the dry analytical elements useful in this invention have at least one porous spreading zone (which can also be a spreading/reagent zone containing the reagent composition). This zone can be a self-supporting carrier matrix (i.e. composed of a material rigid enough to maintain its integrity), but preferably it is carried on a separate support. Such a support is a substrate made of any suitable dimensionally stable, and preferably. transparent (i.e. radiation transmissive) material which transmits electromagnetic radiation of a wavelength between about 200 and 900 nm. Useful support materials include polystyrene, polyesters [e.g. poly(ethylene terephthalate)], polycarbonates, cellulose esters, etc. The element can have a single zone or a plurality of zones (spreading, spreading/reagent, reagent, subbing, mordant, hydrophilic, buffer, etc.), some or all containing reagents. These zones are in fluid contact with each other, meaning that fluids can pass between superposed regions of adjacent zones. Stated in another manner, fluid contact refers to the ability to transport components of a fluid between the zones in fluid contact. Preferably, the zones are separate coated layers, although one or more zones can be in a single layer, or one or more separate layers can be in a single zone, of an element. Dry element formats and materials are known in the art and described, for example, in U.S. Pat. Nos. 3,992,158 (issued November 16, 1976 to Przybylowicz et al); 4,042,335 (issued August 16, 1977 to Clément); 4,144,306 (issued March 13, 1979 to Figueras); 4,132,528 (issued January 2, 1979 to Eikenberry et al); and 4,258,001 (issued March 24, 1981 to Pierce et al), the disclosures of which are incorporated herein by reference in their entirety.

The porous spreading zone in preferred elements is generally a layer which can accept (i.e. absorb completely) an aqueous liquid sample of at least about 1 µL. When the sample is applied directly to the zone or provided to it from a zone or zones in fluid contact with it, the sample is distributed such that a uniform concentration of the sample is provided at the surface of the spreading zone facing an adjacent zone. Useful materials for preparing spreading zones are described, for example, in U.S. Pat. Nos. 3,992,158 and 4,258,001, noted hereinabove; and 4,292,272 (issued September 29, 1981 to Kitajima et al); West German OLS 3,150,102 (published July 29, 1982); and Japanese Patent Publication 57(1982)-101760 (published June 24, 1982). The spreading zone, for example, can be composed of either fibrous or non-fibrous materials, or both. Preferably, the spreading zone is a nonfibrous, isotropically porous spreading layer including a blush polymer as described in U.S. Pat. No. 3,992,158, noted hereinabove. It is desirable that the spreading zone be translucent when wet. In a translucent spreading zone, whether observed visually or by means of a spectrophotometer, all of the azobilirubin which is produced, even that which is deep within the zone, is detectable. Useful spreading layers which are translucent when wet include layers containing Avicel ® or barium sulfate and the bead spreading layer of U.S. Pat. No. 4,258,001, noted hereinabove. These layers, when contacted with serum are translucent.

In certain embodiments, the dry analytical element useful in the present invention also includes a hydrophilic zone between the support and the spreading zone. This hydrophilic zone can contain the 3,3-dimethylglutaric acid buffer, if desired and therefore serve as a buffer zone. This zone includes a binder material which can be any of a wide variety of hydrophilic film-forming materials, such as gelatin, agarose or hydrophilic synthetic polymers such as polyacrylamides, acrylamide-vinyl pyrrolidone copolymers, or mixtures of any such materials.

In other embodiments, the elements of this invention comprise a support having thereon, in order and in fluid contact, a hydrophilic zone, a buffer zone and a spreading zone. The buffer zone contains the 3,3-dimethylglutaric acid (or equivalent salt thereof) buffer in the appropriate amount. The diazonium salt can be in any of the zones, but is preferably in the spreading zone. As noted hereinabove, each zone can be a separate coated layer, or two or more zones can be in a single coated layer.

Preferred elements of this invention also contain a mordant for azobilirubin in either or both of the above-described hydrophilic or buffer zones. Alternatively, the mordant can be in a separate mordant zone. Such mordants are cationic in nature. Particularly useful mordants are described in U.S. Pat. Nos. 4,069,017 (issued January 17, 1978 to Wu et al) and 4,204,839 (issued May 27, 1980 to Wu et al), the disclosures of which are incorporated herein by reference. A preferred mordant is poly(styrene-co-N-vinylbenzyl-N-benzyl-N,N-dimethylammonium chloride-co-divinylbenzene).

One or more zones (e.g. reagent, spreading, subbing, hydrophilic, buffer, mordant, etc.) of the elements of this invention can contain a variety of one or more surfactants, binders (generally hydrophilic natural or synthetic colloids or polymers), hardeners, etc. These components are present in amounts known in the clinical chemistry art.

A variety of different elements can be prepared and used in accordance with the present invention. Elements can be configured in a variety of forms, including elongated tapes of any desired width, sheets or chips.

The analytical method of this invention can be manual or automated. In general, the amount of total bilirubin in an aqueous liquid is determined by taking an element from a supply roll, slide packet or other source and physically contacting it with a sample of the liquid. Such contact can be accomplished in any suitable manner, e.g. dipping or immersing the element into the sample or, preferably, by spotting the element by hand or machine with a drop (e.g. about 1–20 µL) of the sample by pipette or another suitable dispensing means.

After sample application, the element is exposed to any conditioning, such as incubation, heating or the like, that may be desirable to quicken or otherwise facilitate obtaining any test result.

The bilirubin, if present, then reacts with the diazonium salt (or diazo reagent) and produces azobilirubin fairly quickly, which end product is quantifiable by passing the element through a zone in which suitable apparatus for colorimetric detection (reflection or transmissive spectrophotometry) is provided.

The amount of azobilirubin formed as a result of the reaction of bilirubin with the diazonium salt is colorimetrically measured with conventional spectrophotometric apparatus by determining the absorbance at a particular wavelength or a set of two or more wavelengths. The specific wavelength (e.g. 540 $\lambda_{max}$) used in the method depends upon the diazonium salt used.

One particularly useful analytical method for measuring the azobilirubin formed is described in copending and commonly assigned U.S. patent application Ser. No. 597,878 filed by my colleagues, D. H. Lo, M. W. Bailey, and myself on even date herewith, and entitled METHOD AND APPARATUS FOR DETERMINATION OF AN ANALYTE AND METHOD OF CALIBRATING SUCH APPARATUS. The method described therein is a multiple (e.g. two) wavelength measurement technique which provides further assurance of accuracy in the practice of the present invention.

The following examples are presented to illustrate the practice of this invention. In these examples, the sources of materials were as follows: polyurethane resin as Estane ™ 5715 from B. F. Goodrich Co. (Cleveland, Ohio); dyphylline from Aldrich Chemicals Co. (Milwaukee, Wisconsin); Triton ™ X-100 surfactant from Rohm & Haas (Philadelphia, Pennsylvania); Surfactant 10G ™ from Olin Mathieson Corp. (Stamford, Connecticut); and the remainder from Eastman Organic Chemicals (Rochester, New York).

Manual solution assays were carried out on a conventional Perkin-Elmer spectrophotometer. Automated solution assays were carried out on a Rotochem ™

IIa-36 centrifugal analyzer obtained from American Instrument Co., Silver Springs, Maryland.

EXAMPLE 1

Total Bilirubin Solution Assay

This is an example comparing the method of this invention carried out in solution to a state-of-the-art bilirubin assay, also done in solution. The data presented hereinbelow illustrate the improvement in accuracy provided by the present invention. The inaccuracy of the known assay exhibited with some serum samples was due to an unknown interferent. The present invention overcomes that inaccuracy.

Several serum samples, including some from uremic patients were assayed for total bilirubin using three different methods, that of this invention, a control method and a reference method.

A reference assay was carried out using the conventional Jendrassik-Gróf diazo method and reagents described in *Fundamentals of Clinical Chemistry*, Tietz (Ed.), 2nd Ed., W. B. Saunders Co., Philadelphia, 1976, pp. 1037–1040. The diazo reagent and buffer used in that reference method were mixed with the serum samples, and the resulting azobilirubin fragments were determined by measuring the reflectance density at 600 nm with the Rotochem TM clinical chemistry analyzer. The data obtained were used as reference data. No positive bias was observed at this wavelength.

The control A assay was carried out according to the teaching of U.S. Pat. No. 4,468,467 noted hereinabove. The reagent composition comprised 4-(N-carboxymethylsulfamyl)benzenediazonium hexafluorophosphate (5 mg/dL), dyphylline (5 mg/dL) and malic acid sufficient to buffer the composition at pH 5. After mixing the reagents with the serum samples, the resulting azobilirubin fragments in each sample were determined by measuring the reflectance density at 540 nm using the conventional Perkin-Elmer spectrophotometer.

The assay of this invention was carried out like Control A except that the reagent composition comprised about 0.2 M 3,3-dimethylglutaric acid, sodium salt.

In each of the assays, about 0.1 mL of serum sample was mixed with the appropriate reagents. All serum samples were tested twice. Table I below lists the total bilirubin (mg/dL) values for the samples for each assay.

TABLE I

| Sample | Total Bilirubin (mg/dL) | | |
|---|---|---|---|
| | Reference | Control A | Example 1 |
| 1 | 1.0 | 1.03 | 1.00 |
| 2 | 2.0 | 2.05 | 2.02 |
| 3 | 5.0 | 5.08 | 5.04 |
| 4 | 0.2 | 0.89 | 0.22 |
| 5 | 0.2 | 0.98 | 0.25 |
| 6 | 0.3 | 1.50 | 0.40 |
| 7 | 0.7 | 1.28 | 0.61 |

These data demonstrate that the state-of-the-art assay, Control A, and the assay of this invention correlate well with the reference assay for the non-uremic samples 1–3. However, Control A is significantly inaccurate on the positive side with the uremic serum samples 4–7. The assay of this invention, however, correlates well with the reference assay and therefore provides significantly greater accuracy for those uremic samples over Control A.

EXAMPLE 2

Total Bilirubin Solution Assay Comparison Utilizing Different Diazonium Salts This is also a comparative example. Two pooled uremic serum samples from a number of human patients were tested for total bilirubin content using the reference and Control A assays of Example 1 as well as the other assays described below.

Control B was carried out like the reference assay except that the azobilirubin fragments were measured in test tubes using a conventional Perkin-Elmer spectrophotometer instead of the Rotochem TM analyzer.

Control C was carried out like the reference assay except that the alkaline tartrate step which causes a shift of the wavelength to 600 nm was eliminated. Hence, the resulting azobilirubin fragments were measured at 540 nm.

Control D was carried out according to the method described by Malloy and Evelyn in *J. Biol. Chem., 119,* p. 481 (1937). The diazo reagent used included diazotized 2,4-dichloroaniline.

The total bilirubin data presented in Table II hereinbelow indicate that the unknown interferent affects the accuracy of all of the assays tested at 540 nm except that of the present invention. Little interference is observed with Control B because therein the wavelength is shifted to 600 nm where the interferent has relatively little effect. The assay of this invention provides substantial improvement at shorter wavelengths, e.g. 540 nm where the effect of the interferent is more pronounced.

TABLE II

| Assay | Total Bilirubin (mg/dL) | |
|---|---|---|
| | Pool 1 | Pool 2 |
| Reference | 0.30 | 0.54 |
| Control A | 0.98 | 1.30 |
| Control B | 0.29 | 0.41 |
| Control C | 0.69 | 0.88 |
| Control D | 0.78 | 0.90 |
| Example 1 | 0.33 | 0.52 |

EXAMPLE 3

Total Bilirubin Assay Using Dry Analytical Elements

This example compares the present invention as practiced with a dry of analytical element of this invention to the assay of U.S. Pat. No. 4,468,467, noted hereinabove, utilizing elements (identified as Controls) taught therein outside the scope of the present invention. The Control elements used acids other than 3,3-dimethylglutaric acid, or acids to maintain a pH above 3.5, or both.

Dry elements having the following format and components were prepared:

| Element Format I | | |
|---|---|---|
| Spreading/ Reagent Layer | Cellulose acetate | 4–12 g/m$^2$ |
| | Estane TM 5715 polyurethane resin | 0.5–5 g/m$^2$ |
| | Barium sulfate | 50–150 g/m$^2$ |
| | Triton TM X-100 surfactant | 0.5–5 g/m$^2$ |
| | Dyphylline | 1–10 g/m$^2$ |
| | 4-(N—carboxymethylsulfamyl)- benzenediazonium hexa- fluorophosphate | 0.2–2 g/m$^2$ |
| Subbing Layer | Poly(N—isopropylacryl- amide) | 0.1–3 g/m$^2$ |
| Hydrophilic | Poly(acrylamido-co-N— | 2–12 g/m$^2$ |

-continued

| | Element Format I | |
|---|---|---|
| Buffer Layer | vinyl-2-pyrrolidone) (50:50 weight ratio) Triton TM X-100 surfactant Buffer* Poly(ethylene terephthalate) Support | 0.5–5 g/m² 1–7.5 g/m² |

*See Table III hereinbelow.

Element Format II

This element was like Element Format I except that Surfactant 10G TM was used in the hydrophilic buffer layer in place of Triton TM X-100. This format (i.e. II) was used for Control F. Element Format I was used for all other controls and for the element of this invention.

Samples of each element were used to determine total bilirubin in serum samples obtained from 10 uremic patients. Table III below presents the data obtained from such evaluations using various buffers at different pHs. It is apparent that the element of this invention containing 3,3-dimethylglutaric acid, sodium salt, and buffered at pH 3.0, provided significant improvement in the accuracy of the bilirubin determination over similar elements outside the scope of this invention. Only the element of this invention eliminated the bias in all samples.

TABLE III

| Element | Buffer | pH | # of Inaccurate Datum Points Removed* |
|---|---|---|---|
| Control A | Malic acid | 5.0 | None |
| Control B | Tartaric acid | 3.0 | 5 out of 10 |
| Control C | Phthalic acid | 3.0 | 3 out of 10 |
| Control D | Maleic acid | 2.0 | 5 out of 10 |
| Control E | Malic acid | 5.0 | None |
| Control F | 3,3-dimethyl-glutaric acid | 5.0 | 3 out of 10 |
| Example 3 | 3,3-dimethyl-glutaric acid | 3.0 | 10 out of 10 |

*An inaccurate datum point refers to a total bilirubin test value which is greater than 1 as compared to a predicted total bilirubin value of 1 as determined using the same test serum sample and the Jendrassik-Grof reference method modified as described by Perry et al in Clin. Chem., 29, pp. 297–301 (1983).

EXAMPLE 4

Dry Analytical Element Containing Mordant Layer

A dry analytical element was prepared according to the present invention having the following format and components:

| | | |
|---|---|---|
| Spreading/ Reagent Layer | Cellulose acetate Estane TM 5715 polyurethane Barium sulfate Triton TM X-100 surfactant Dyphylline 4-(N—carboxymethylsulfamyl)-benzenediazonium hexafluorophosphate | 4–12 g/m² 0.5–5 g/m² 50–150 g/m² 0.5–5 g/m² 1–10 g/m² 0.2–2 g/m² |
| Subbing Layer | Poly(N—isopropylacryl-amide) | 0.1–3 g/m² |
| Buffer Layer | Poly(acrylamido-co-N—vinyl-2-pyrrolidone) (50:50 weight ratio) Triton TM X-100 surfactant 3,3-dimethylglutaric acid, sodium salt (pH 3) | 2–12 g/m² 0.5–5 g/m² 1–7.5 g/m² |
| Mordant Layer | Gelatin Hardner Surfactant 10G TM surfactant Poly(styrene-co-N—vinyl-benzyl-N—benzyl-N,N—dimethylammonium chloride-co-divinylbenzene) Poly(ethylene terephthalate) Support | 2–12 g/m² 0.02–0.2 g/m² 0.05–1 g/m² 0.2–2.5 g/m² |

Samples of this element were used to accurately determine total bilirubin in uremic serum samples. They compared favorably to the reference assay of the same serum samples described in Example 1 hereinabove.

The invention has been described in detail with particular reference to preferred embodiments thereof, but it will be understood that variations and modifications can be effected within the spirit and scope of the invention.

I claim:

1. A reagent composition comprising a diazonium salt or reagents capable of producing a diazonium salt when contacted with water, and 3,3-dimethylglutaric acid or a salt thereof present in an amount effective to buffer said composition at a pH of about 3.5 or less when contacted with a 2 μL sample of pooled human serum.

2. The reagent composition of claim 1 wherein said diazonium salt is represented by the structure:

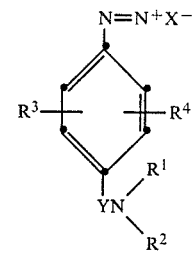

wherein $X^-$ is a stabilizing anion; Y is —CO— or —SO$_2$—; $R^1$ and $R^2$ are independently selected from hydrogen, alkyl, aralkyl, aryl carboxyalkyl and hydroxyalkyl; and $R^3$ and $R^4$ are independently selected from groups such that the sum of the Hammett sigma values for $R^3$ and $R^4$ does not exceed +0.4 or $R^3$ and $R^4$, taken together, represent the carbon atoms necessary to complete a fused carbocyclic arylene moiety.

3. The reagent composition of claim 2 wherein $X^-$ is an anion of a Lewis acid coordinatively saturated by a hydrogen halide, Y is —SO$_2$—, $R^1$ is hydrogen and $R^2$ is carboxymethyl.

4. The reagent composition of claim 3 wherein said diazonium salt is 4-(N-carboxymethylsulfamyl)benzenediazonium hexafluorophosphate.

5. An aqueous reagent solution comprising a diazonium salt buffered at a pH of 3.5 or less with at least about 0.01 M of 3,3-dimethylglutaric acid or a salt thereof.

6. The reagent solution of claim 5 wherein said acid or salt thereof is present at from about 0.05 M to about 0.5 M.

7. A dry analytical element for the determination of total bilirubin in an aqueous liquid, said element comprising a carrier matrix and a reagent composition comprising a diazonium salt or reagents capable of producing a diazonium salt when contacted with water, and 3,3-dimethylglutaric acid or a salt thereof present in an amount effective to buffer said composition at a pH of 3.5 or less when contacted with a 2 μL sample of pooled human serum.

8. The element of claim 7 wherein said diazonium salt is represented by the structure:

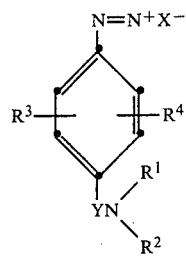

wherein X⁻ is a stabilizing anion, Y is —CO— or —SO₂—; R¹ and R² are independently selected from hydrogen, alkyl, aralkyl, aryl, carboxyalkyl and hydroxyalkyl; and R³ and R⁴ are independently selected from groups such that the sum of the Hammett sigma values for R³ and R⁴ does not exceed +0.4 or R³ and R⁴ taken together, represent the carbon atoms necessary to complete a fused carbocyclic arylene moiety.

9. A dry analytical element for the determination of total bilirubin in an aqueous liquid, said element comprising: a support having thereon a porous spreading zone;

said spreading zone containing a reagent composition comprising a diazonium salt or reagents capable of producing a diazonium salt when contacted with water, said salt represented by the structure:

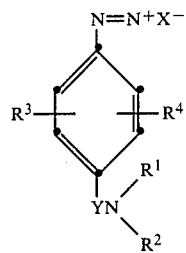

wherein
X⁻ is a stabilizing anion; Y is —CO— or —SO₂—; R¹ and R² are independently selected from hydrogen, alkyl, aralkyl, aryl, carboxyalkyl and hydroxyalkyl; and R³ and R⁴ are independently selected from groups such that the sum of the Hammett sigma values for R³ and R⁴ does not exceed +0.4 or R³ and R⁴, taken together, represent the carbon atoms necessary to complete a fused carbocyclic arylene moiety, and 3,3-dimethylglutaric acid or a salt thereof present in an amount effective to buffer said composition at a pH of about 3.5 or less when contacted with a 2 μL sample of pooled human serum.

10. The element of claim 9 wherein X⁻ is an anion of a Lewis acid coordinatively saturated by a hydrogen halide, Y is —SO₂—, R¹ is hydrogen and R² is carboxymethyl.

11. The element of claim 10 wherein said diazonium salt is 4-(N-carboxymethylsulfamyl)benzenediazonium hexafluorophosphate.

12. A dry analytical element for the determination of total bilirubin in an aqueous liquid, said element comprising: a support having thereon, in order and in fluid contact, a hydrophilic layer containing 3,3-dimethylglu-taric acid or a salt thereof present in an amount effective to buffer said hydrophilic layer at a pH of about 3.5 or less when contacted with a 2 μL sample of pooled human serum, and an isotropically porous spreading-/reagent layer containing a diazonium salt or reagents capable of producing a diazonium salt when contacted with water, said salt represented by the structure:

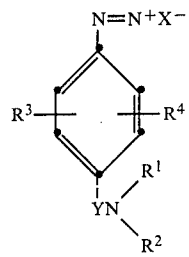

wherein X⁻ is a stabilizing anion; Y is —CO— or —SO₂—; R¹ and R² are independently selected from hydrogen, alkyl, aralkyl, aryl, carboxyalkyl and hydroxyalkyl; and R³ and R⁴ are independently selected from groups such that the sum of the Hammett sigma values for R³ and R⁴ does not exceed +0.4 or R³ and R⁴, taken together, represent the carbon atoms necessary to complete a fused carbocyclic arylene moiety.

13. The element of claim 12 wherein said hydrophilic layer comprises a mordant.

14. The element of claim 12 wherein said diazonium salt is selected from the group consisting of:
4-(N-carboxymethylsulfamyl)benzenediazonium hexafluorophosphate;
4-[N,N-bis(carboxymethyl)sulfamyl]benzenediazonium hexafluorophosphate;
4-[N,N-bis(2-hydroxyethyl)sulfamyl]benzenediazonium hexafluorophosphate;
4-(N-carboxymethylcarbamyl)benzenediazonium tetrafluoroborate;
4-(N-carboxypropylcarbamyl)benzenediazonium naphthylenedisulfonate;
4-(N-carboxymethylsulfamyl)benzenediazonium tetrafluoroborate;
4-(N-dodecylsulfamyl)benzenediazonium tetrafluoroborate;
3,5-dichloro-4-(N-carboxymethylsulfamyl)benzenediazonium hexafluorophosphate;
4-(N-carboxymethylsulfamyl)-1-diazonium naphthylene hexafluorophosphate;
7-[N-tris(hydroxymethyl)methylcarbamyl]-4-diazoniumindene hexafluorophosphate; and
4-[N,N-bis(carboxymethyl)sulfamyl]-1-diazonium-6-methoxy naphthylene chlorozincate.

15. The element of claim 12 wherein said acid or salt thereof is present in a coverage of from about 1 to about 7.5 g/m².

16. The element of claim 12 wherein said acid or salt thereof is present in an amount effective to buffer said hydrophilic layer at a pH of from about 1 to about 3.5 when contacted with a 2 μL sample of pooled human serum.

17. A method for determination of total bilirubin in an aqueous liquid, said method comprising the steps of:
(A physically contacting a sample of said liquid with a reagent composition comprising:
a diazonium salt or reagents capable of producing said salt when contacted with water; and 3,3-dimethylglutaric acid or a salt thereof present in an amount effective to buffer said composition at a pH of 3.5 or less when contacted with a 2 μL sample of pooled human serum; and (B) colorimetrically measuring the amount of azobilirubin formed as a result of said contact.

18. The method of claim 17 wherein said diazonium salt is represented by the structure:

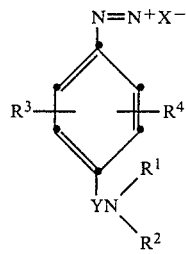

wherein $X^-$ is a stabilizing anion; Y is —CO— or —SO$_2$—; $R^1$ and $R^2$ are independently selected from hydrogen, alkyl, aralkyl, aryl, carboxyalkyl and hydroxyalkyl; and $R^3$ and $R^4$ are independently selected from groups such that the sum of the Hammett sigma values for $R^3$ and $R^4$ does not exceed +0.4 or $R^3$ and $R^4$, taken together, represent the carbon atoms necessary to complete a fused carbocyclic arylene moiety.

19. The method of claim 17 wherein said sample is contacted with a dry analytical element comprising a support having thereon, in order and in fluid contact, a hydrophilic layer containing said acid and a spreading-/reagent layer containing said diazonium salt.

20. The method of claim 19 wherein said hydrophilic layer comprises a mordant.

* * * * *